United States Patent [19]

Kramer et al.

[11] Patent Number: 4,676,880
[45] Date of Patent: Jun. 30, 1987

[54] PHOTOLYSIS OF LACTONES

[75] Inventors: David N. Kramer, Stevenson; Thomas N. Oeltmann, Edgewood Arsenal, both of Md.

[73] Assignee: The United States of America as represented by the Secretary of the Army, Washington, D.C.

[21] Appl. No.: 830,221

[22] Filed: May 29, 1969

[51] Int. Cl.[4] .............................................. B01J 19/12
[52] U.S. Cl. .................................. 204/157.91; 204/901
[58] Field of Search ................. 204/157.1 R, 158.1 R, 204/160.1, 157.91, 901; 23/230 R

[56] References Cited

U.S. PATENT DOCUMENTS 3,382,239  5/1968  Barton ................................. 204/158
3,401,106  9/1968  Elad et al. ........................... 204/158

OTHER PUBLICATIONS

Defensive Publication published Jan. 21, 1969, 858 O.G. 725, Vermont G.B., filed 8/68.

Primary Examiner—John F. Terapane
Assistant Examiner—John S. Maples
Attorney, Agent, or Firm—Anthony T. Lane; Robert P. Gibson; Harold H. Card, Jr.

[57] ABSTRACT

The photochemical decarbonylation of lactones and the method of detecting microquantities of $\alpha,\alpha$-diarylglycolate esters comprising an acidic reaction mixture containing the esters and naphthols producing a lactone, decarbonylating the lactone by irradiation and forming a colored solution.

6 Claims, No Drawings

PHOTOLYSIS OF LACTONES

DEDICATORY CLAUSE

The invention described herein may be manufactured, used, and licensed by or for the Government for governmental purposes without the payment to us of any royalty thereon.

This invention relates to a new method for the determination of toxic compounds in the general class of diarylglycolate esters. With our new colorimetric determination, one can ascertain the proportion of the compounds in the range of 0.3 gamma/ml.

It is an object of this invention to employ photochemical decarbonylation of lactones.

It is the further object of this invention to utilize photochemical decarbonylation of lactones to form the visible colored carbonium ion of ortho-naphthofuchsone as the detector signal for the presence of toxic compounds.

There are no known published methods for the direct detection of the toxic compound 3-quinuclidyl diphenylglycolate and its related esters. There are published methods for the 4.0 µg/ml detection level of glycolic acid and other α-hydroxy acids utilizing the reaction of the acid with 2,7-dihydroxynaphthalene in concentrated sulfuric acid giving rise to a red-colored product, Eigrieve, E., *Z. Anal. Chem.*, 89, 121 (1932); Green, H., *Analyst*, 82, 107 (1957).

The prior art indirect methods discussed, supra, were not of sufficient sensitivity for our purposes. An investigation was instituted to seek new direct processes capable of detecting smaller quantities of highly toxic materials. As a result of our work, it is now feasible to indicate the presence of 0.3 µg/ml of toxic compounds. Our method has increased the sensitivity level of detecting by a factor of at least 13, that is, 4.0 µg/ml to 0.3 µg/ml.

One of the advantages of the present invention is that it provides an accurate and highly sensitive method which can be employed in the field under combat conditions for the determination of microquantities of highly toxic compounds in view of the fact that the red color detector signal is visible to the naked eye.

The photochemical decarbonylation of 2-hydroxynaphthyl-1-diphenylacetic acid lactone in the 2500 Å to 3100 Å range requires a reaction medium with the acid concentration between 33 to 50%.

Other various diphenylacetic acid lactones that undergo photochemical decarbonylation according to the irradiation step in this invention are 2,4-dihydroxyphenyl-1,5-di-(di-phenylacetic acid) di lactone, 2,5-dihydroxyphenyl-1-di-phenylacetic acid lactone or 1-diphenylacetic acid-m-cresol lactone.

EXAMPLE 1

(a) A solution comprising about $10^{-2}$M of 2,4-dihydroxyphenyl-1,5-di-(diphenylacetic acid) di lactone and sulfuric acid in a final concentration of 33% to 50% was irradiated in the 2500 Å to 3100 Å range for at least 3 minutes whereby the lactone was decarbonylated as follows

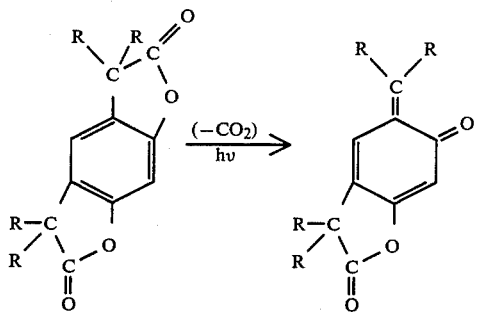

R is a phenyl group

The photochemical decarbonylation in the 2500 Å to 3100 Å range is accomplished by immersing a photochemical quartz lamp (Ultra Violet Products; San Gabriel, Calif., Model #SCT-1) into the reaction matrix for the required time period.

(b) The procedure in (a), supra, was repeated with the substitution of lactones selected from the group consisting of 2-hydroxynaphthyl-1-diphenylacetic acid lactone, 2,5-di-hydroxyphenyl-1-diphenylacetic acid lactone and 1-diphenylacetic acid-m-cresol lactone for the corresponding lactone giving rise to the similar decarbonylated lactones.

The kinetic studies in Table I, below, were carried forward in accordance with the procedure in "Kinetic Reactions in Solution", E. A. Moelwyn-Hughes, Clarendon Press, 1947, page 267.

TABLE I

| Lactone | [1]Decarbonylation Rates, min$^{-1}$ |
| --- | --- |
| 2-hydroxynaphthyl-1-diphenyl-acetic acid lactone | $2.93 \times 10^{-3}$ |
| 2,4-dihydroxyphenyl-1,5-di-(diphenylacetic acid) di lactone | $7.6 \times 10^{-3}$ |
| 2,5-dihydroxyphenyl-1-diphenyl-acetic acid lactone | $5.92 \times 10^{-3}$ |
| 1-diphenylacetic acid-m-cresol lactone | very slow |

[1]The rates are independent of solvent, however we utilized acetone in these studies. Other solvents may be diethylether, benzene or sulfuric acid.

The α-α-diarylglycolate esters procedure for detection may be achieved by initially mixing all the components or by sequential component addition as illustrated in the general scheme below.

A solution comprising diarylglycolate esters is reacted with a naphthol in the presence of concentrated sulfuric acid and solvent forming a lactone, Compound I, in situ, in the reaction solution. The reaction solution is photolyzed between 2500 Å to 3100 Å for 3 to 5 minutes employing a quartz lamp, thus converting the lactone I in the presence of sulfuric acid to ortho-naphthofuchsone, Compound II, which is converted to its corresponding visible red-colored carbonium ion, Compound III or the solution may be read optically at 450 millimicrons for a more exact concentration level.

GENERAL SCHEME

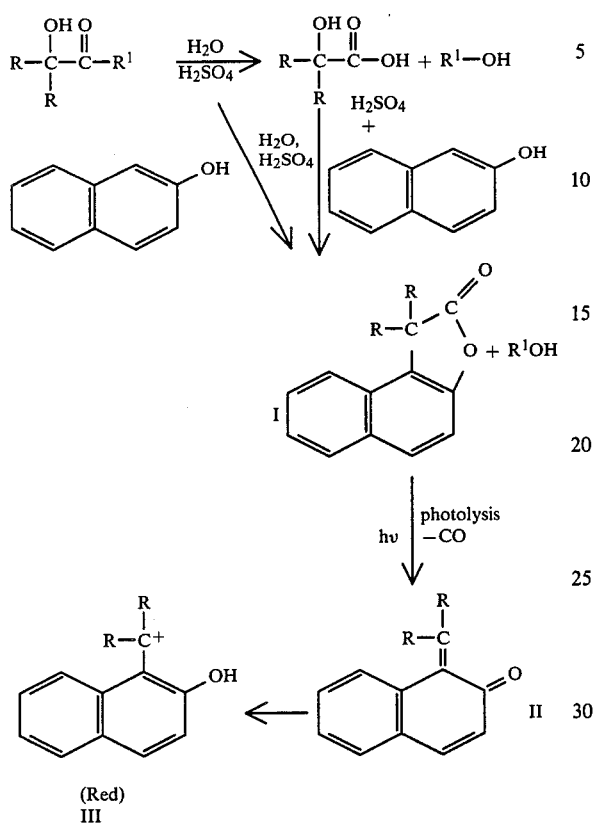

Wherein:
R is phenyl group
R' is methy, ethyl or quinuclidinyl group

The solvents in this detection method may be any aliphatic carboxylic acid from $C_2$ to $C_4$ carbon atoms such as glacial acetic, propionic acid or butyric acid.

EXAMPLE 2

A sample comprising 3-quinuclidinyl diphenylglycolate, methyl diphenylglycolate or ethyl diphenylglycolate is reacted in an acidic mixture comprising $5 \times 10^{-3}$ to $5 \times 10^{-2}$M β-naphthol in $C_2$ to $C_4$ aliphatic carboxylic acid and sulfuric acid in a concentration of 33% to 50% in the final reaction mixture forming a lactone I, in situ. The mixture comprising the lactone is subjected to photolysis in the 2500 Å to 3100 Å range for at least 3 minutes in order to decarbonylate the lactone to ortho-naphthofuchsone II, forming the corresponding carbonium ion giving rise to a red colored solution indicating the presence of at least 0.3 μg/ml of the glycolate.

EXAMPLE 3

(a) A reaction mixture comprising mixing 3-quinuclidinyl diphenylglycolate with 50% aqueous sulfuric acid solution, then adding about $5 \times 10^{-3}$ to $5 \times 10^{-2}$M β-naphthol in glacial acetic acid and sulfuric acid (98%), the concentration of the acid is between 33% and 50% in the final reaction mixture. The mixture is irradiated in the 2500 Å to 3100 Å range for at least 3 minutes, thus decarbonylating lactone I to the ortho-naphthofuchsone II, yellow, which in the presence of the sulfuric acid forms the corresponding colored carbonium ion which is read at 450 millimicrons and is visible, thus indicating at least 0.3 μg per ml of the glycolate is present.

(b) The method in (a), supra, was repeated with the substitution of methyl diphenylglycolate or ethyl diphenylglucolate and propionic acid or butyric acid for the corresponding 3-quinuclidinyl diphenylglycolate and glacial acetic acid respectively, giving rise to similar results.

Pharmacological evaluation of the 3-quinuclidinyl di-phenylglycolate for potency was determined by administering intravenously various proportions (mg/kg) of the compound in mice using the method described in "The Search For and Selection of Toxic Chemical Agents for Weapons Systems", disclosed in the Edgewood Arsenal, Maryland Publication (CRDL SOP 70-3, 6 May 1965). $LD_{50}$ is the lowest dose in milligrams of compound per kilogram of animal required to be lethal in 50% of the tested animals. $MED_{50}$ is the minimum dose in milligrams of compounds per kilogram of animal required to give any physiological effect (e.g. mydriasis or increased activity) in 50% of the tested animals. The quotient of the ratio $LD_{50}MED_{50}$ is the margin of safety, that is the higher numerical quotient, the greater the amount of agent can be used before causing death.

The values for 3-quinuclidinyl diphenylglycolate are $LD_{50} = 15.8$; $MED_{50}$ (mydriasis) $= 0.0178$; $LD_{50}/MED_{50} = 890$.

EXAMPLE 4

(a) Into a 500 ml round bottom 3-neck flask equipped with a modified Dean-Stark water separator, a dropping funnel, a Hershberg stirrer and a thermometer were added, in order, methyl benzilate (19.4 g; 0.08 moles), 3-quinuclidinol (10.7 g; 0.084 moles), sodium dried n-heptane (300 ml), and small lumps of metallic sodium (0.13 g.; 0.0057 g. atoms). All openings to the atmosphere were protected by drying tubes filled with a layer of dehydrated silica gel or "Drierite" (i.e. anhydrous calcium sulfate) and a layer of sodium hydroxide pellets. The vigorously stirred reaction mixture was heated to reflux in an oil bath. At about the time the n-heptane methanol azeotrope started to distill, practically all of the reactants had dissolved. The azeotrope was collected as it distilled. After 15 minutes of reflux time, about 1.3 to 3.2 ml of methanol was collected. After approximately 30 minutes, 2.2 ml of the methanol was collected and the while solid product began to percipitate. The Dean-Stark separator was then permitted to fill and most of the distillate was allowed to return to the reaction flask. The azeotrope was removed slowly from the Dean-Stark apparatus at a rate of about 0.15 ml per minute. During the reaction period, the volume of the mixture was kept constant by the addition of n-heptane from the dropping funnel. A total of approximately 50 ml of distillate was removed. After four hours, the reaction was stopped and the mixture cooled to 20° C. As far as it could be determined the theoretical quantity of methanol was collected. The white crystalline solid product was collected on a Buckner funnel, was thoroughly washed with several 20 ml portions of water, dried in vacuo over phosphorus pentoxide. The dried product was 3-quinuclidinyl diphenylglycolate.

(b) The method in (a), supra, was repeated but substituting methyl alcohol or ethyl alcohol for the 3-quinuclidinol giving rise to methyl diphenylglycolate or ethyl diphenylglycolate.

As a result flowing from our invention, a sample, in a hostile environment, suspected of comprising toxic materials can be determined by the simple addition of a naphthol in a solvent and sulfuric acid with subsequent photolysis and visual color indication of the presence of the toxic materials in a total time of about 5 minutes or less. This small time frame is of utmost importance in determining whether or not the soldiers are in a contaminated area.

We claim:

1. A process of detecting $\alpha, \alpha$-diarylglycolate esters the steps comprising reacting said esters in an acidic medium with naphthols in a solvent producing lactones in the medium, said medium having an acid concentration between 33 to 50%, irradiating between 2500 Å–3100 Å the lactones in the acid medium for at least 3 minutes, and decarbonylating the lactones forming a visible colored solution.

2. The process according to claim 1, wherein the esters are a member selected from the group consisting of 3-quinuclidinyl diphenylglycolate, methyl diphenylglycolate and ethyl diphenylglycolate.

3. The process according to claim 1, wherein the solvent is an aliphatic carboxylic acid from $C_2$ to $C_4$ carbon atoms.

4. The process according to claim 1, wherein the steps comprising adding said esters to the acidic medium forming $\alpha,\alpha$-diarylglycolic acids and reacting the latter acids with naphthols in a solvent producing lactones in the medium.

5. The process according to claim 4, wherein the esters are a member selected from the group consisting of 3-quinuclidinyl diphenylglycolate, methyl diphenylglycolate and ethyl diphenylglycolate.

6. The process according to claim 4, wherein the solvent is an aliphatic carboxylic acid from $C_2$ to $C_4$ carbon atoms.

* * * * *